US00PP13491P3

(12) United States Plant Patent

Olesen et al.

(10) Patent No.: US PP13,491 P3
(45) Date of Patent: Jan. 21, 2003

(54) MINIATURE ROSE PLANT NAMED 'POULTY002'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 25 days.

(21) Appl. No.: 09/774,267

(22) Filed: Jan. 29, 2001

(65) Prior Publication Data

US 2002/0152510 P1 Oct. 17, 2002

(51) Int. Cl.[7] ..... A01H 5/00
(52) U.S. Cl. ..... Plt./118
(58) Field of Search ..... Plt./118

(56) References Cited

PUBLICATIONS

UPOV–ROM GTITM Computer Database, 2001/06, GTI Jouve Retrieval Software, citation for 'POULty002'.*

* cited by examiner

*Primary Examiner*—Bruce R. Campell
*Assistant Examiner*—Susan B. McCormick

(57) ABSTRACT

A new miniature rose plant which has abundant, golden-yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Classification

*Botanical.*—*Rosa hybrida* 'POULty002'.

*Commercial.*—Miniature.

SUMMARY OF THE INVENTION

The present invention constitutes a new and distinct variety of miniature rose plant which originated from a controlled crossing between an unnamed seedling, and 'POULjol' both unpatented varieties. The two parents were crossed and the resulting seeds were planted in a controlled environment. The new variety is named 'POULty002'.

The new rose may be distinguished from its seed parent, an unnamed seedling, by the following combination of characteristics:

1. The seed parent has orange-red blooms, whereas 'POULty002' has golden-yellow blooms.
2. The seed parent, as a miniature rose, is taller in growth than 'POULty002'.

The new variety may be distinguished from its pollen parent, 'POULjol' created by the same inventors, by the following combination of characteristics:

1. The pollen parent has clear yellow blooms, whereas 'POULty002' has golden-yellow blooms.
2. 'POULjol' has a larger, bushier habit than 'POULty002'.

The objective of the hybridization of this rose variety for commercial culture was to create a new and distinct variety with unique qualities, such as:

1. Uniform and abundant golden-yellow flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULty002' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark. 'POULty002' was selected by the inventors as a single plant from the progeny of the hybridization in spring 1997.

Asexual reproduction of 'POULty002' by cuttings and traditional budding was first done by L. Pernille and Mogens N. Olesen in their nursery in Fredensborg, Denmark in June 1997. This initial and other subsequent propagations conducted in controlled environments have demonstrated that the characteristics of 'POULty002' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULty002'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULty002', as observed in its growth in glasshouses in Fredensborg, Denmark; and Half Moon Bay, Calif. Color references are made using The Royal Horticultural Society (London, England) Colour Chart, 1995, except where common terms of color are used.

For a comparison, several physical characteristics of the rose variety 'POULgildo', a rose variety from the same inventors described and illustrated in U.S. Plant patent application Ser. No. 09/677,573 dated Sep. 27, 2000 are compared to 'POULty002' in Chart 1.

CHART 1

| | 'POULty002' | 'POULgildo' |
|---|---|---|
| General tonality of flower bloom | Outer petals: Yellow Group 9D<br>Inner petals: Yellow-Orange 18A | Yellow Group 4A–B |
| Bud color at ¼ opening | Yellow-Orange Group 23C–D | Yellow Group 4A |
| Petalage | Double, 25–30 | Double, 34–37 petals |

Parents: Unnamed seedling×'POULjol'.

FLOWER AND FLOWER BUD

Blooming habit: Continuous.

Flower bud:

*Size.*—Upon opening, 20 mm in length from base of receptacle to end of bud. Diameter is 40 mm.

*Bud form.*—Long, pointed-ovoid.

*Bud color.*—As sepals unfold, Orange Group 29D with guard petals having intonations of Yellow-Green 145B–C. Yellow-Orange Group 23C–D at ¼ opening.

*Sepals.*—Green Group 143A. Weak foliaceous appendages on three of the five sepals. Inner surfaces of sepals strongly pubescent. Stipitate glands are present on sepals with foliaceous appendages. Sepals are 10 mm wide and 20 mm long.

*Receptacle.*—Surface: Smooth. Shape: Funnel. Size: Small. 8 mm (h)×6 mm (w). Color: Yellow-Green Group 144B.

*Peduncle.*—Surface: Moderate number of stipitate glands. Length: 15–20 mm average length. Color: Yellow-Green Group 144A. Strength: Erect.

*Borne.*—Singularly. One bud per flowering stem.

*Anthocyanin.*—None.

Flower bloom:

*Fragrance.*—None.

*Duration.*—As a pot plant, flowers last from 12 to 15 days. As a cut flower 4 to 6 days. The blooms have a duration on the plant of approximately 10 to 14 days.

*Size.*—Large for a 6-cm pot rose. Average flower diameter is 40–50 mm when open.

*Form.*—Shape of flower when viewed from the side: Upon opening, upper part: Flat. Upon opening, lower part: Concave. Open flower, upper part: Flattened Convex. Open flower, lower part: Concave.

*Petalage.*—Double. Average range: 25–30 petals under normal conditions with 0–8 petaloids.

Color:

*Upon opening, petals.*—Outermost petals: Outer Side: Yellow-Orange Group 19B. Inner Side: Yellow-Orange Group 20B. Basal zone: Both upper and lower surfaces exhibit intonations of Yellow-Green Group 154B–C. Innermost petals: Color is consistent on both Inner and Outer sides of petals exhibiting a blend of: Marginal zone: Yellow-Orange Group 23D. Middle zone: Yellow Group 11B with intonations of Yellow-Green Group 154C. Basal zone: Yellow-Green Group 154B.

*Upon opening, basal petal spots.*—No distinctive coloration at petal base observed.

*After opening, petals.*—Outermost petals: Outer Side: Yellow Group 12C. Inner Side: Yellow Group 13D with basal zone of petal Yellow Group 13B. Innermost petals: Outer Side: Yellow Group 11B. Inner Side: Yellow Group 12C.

*After opening, basal petal spots.*—No distinctive coloration at petal base observed.

General tonality: On open flower, outer petals: Yellow Group 9D; inner petals: Yellow-Orange Group 18A with intonations of Orange Group 28D. No change in the general tonality at the end of the $8^{th}$ day. Afterwards, general tonality is Yellow-Orange Group 18D.

Petals:

*Size.*—18 mm (l)×15 mm (w).

*Petal reflex.*—Slightly.

*Petal edge.*—Slightly ruffled.

*Shape.*—Deltoid. Apex is entire with occasional notch in center, base is acute.

*Petaloids.*—Present. Quantity: 0–8.

*Thickness.*—Average.

*Arrangement.*—Loosely imbricated.

Reproductive organs:

*Pollen.*—Color: Greyed-Orange Group 167A. Quantity: Very abundant.

*Anthers.*—Size: Medium. Color: Greyed-Orange Group 163A. Quantity: 20 to 25.

*Filaments.*—Color: Yellow-Orange Group 16B.

*Stigmas.*—At same height as anthers. Color: Greyed-Yellow Group 160B.

*Styles.*—Color: Yellow-Green Group 145C. Upper one-half of styles has moderate intonations of Greyed-Red Group 181C.

*Hips.*—Not observed on pot plants.

*Seed production.*—No seed production observed to date.

PLANT

Plant growth: Compact and upright. When grown as a 6-cm pot plant, the average height of the plant is 7–10 cm and the average width is 10–12 cm.

Stems:

*Size.*—Length: 25 to 30 cm. Diameter: 4 mm.

*Color.*—Young wood: Yellow-Green Group 144A. Older wood: Yellow-Green Group 144A.

*Prickles.*—Incidence: Many prickles. Size: Average length: 3–5 mm. Color: Mature: Greyed-Brown Group 199C. Juvenile: Yellow-Green Group 145B with intonations of Greyed-Orange Group 174B. Shape: Concave.

*Surface.*—Young wood: Smooth. Older wood: Smooth.

Plant foliage: Typical number of leaflets on normal leaves in middle of the stem: 5–7 leaflets.

*Leaf size.*—Small. 40–50 mm (l)×30–35 mm (w).

*Quantity.*—Average.

*Color.*—Upper Leaf Surface: Yellow-Green Group 147A. Lower Leaf Surface: Yellow-Green Group 147B. Juvenile foliage: Upper Leaf Surface: Green Group 137A. Lower Leaf Surface: Green Group 137D. Anthocyanin intonation: None.

Plant leaves and leaflets:

*Stipules.*—Size: 8–10 mm (l)×2–3 mm (w). Color: Green Group 143B–C. Presence of stipitate glands: Numerous along margins. Anthocyanin: None.

*Petiole.*—Length: 11–12 mm. Color: Green Group 143A–C. Underneath: Smooth with occasional prickle. Margins: Limited number of stipitate glands. Anthocyanin: None.

*Rachis.*—Color: Green Group 143C. Underneath: Occasional prickle at leaflet joint and a moderate number of stipitate glands. Margins: Few stipitate glands. Anthocyanin: None.

*Leaflet.*—Edge: Serrated. Shape: Broadly ovate. Base is rounded, apex is acute. Other: Glossy and thin. Venation: Reticulate. Vein color is Yellow-Green Group 150A.

Disease resistance: Above average resistance to mildew, black spot, and Botrytis under normal growing conditions in Jackson County, Oreg.

Cold hardiness: The variety 'POULhi001' has been found to be resistant to damage from cold in USDA Zone 7.

We claim:

1. A new and distinct variety of rose plant of the miniature class, substantially as herein illustrated and described as a distinct and novel rose variety due to its abundant, golden-yellow flowers, vigorous growth, compact habit, suitability for production from softwood cuttings in pots, and durable flowers and foliage which make the variety suitable for distribution in the floral industry.

* * * * *

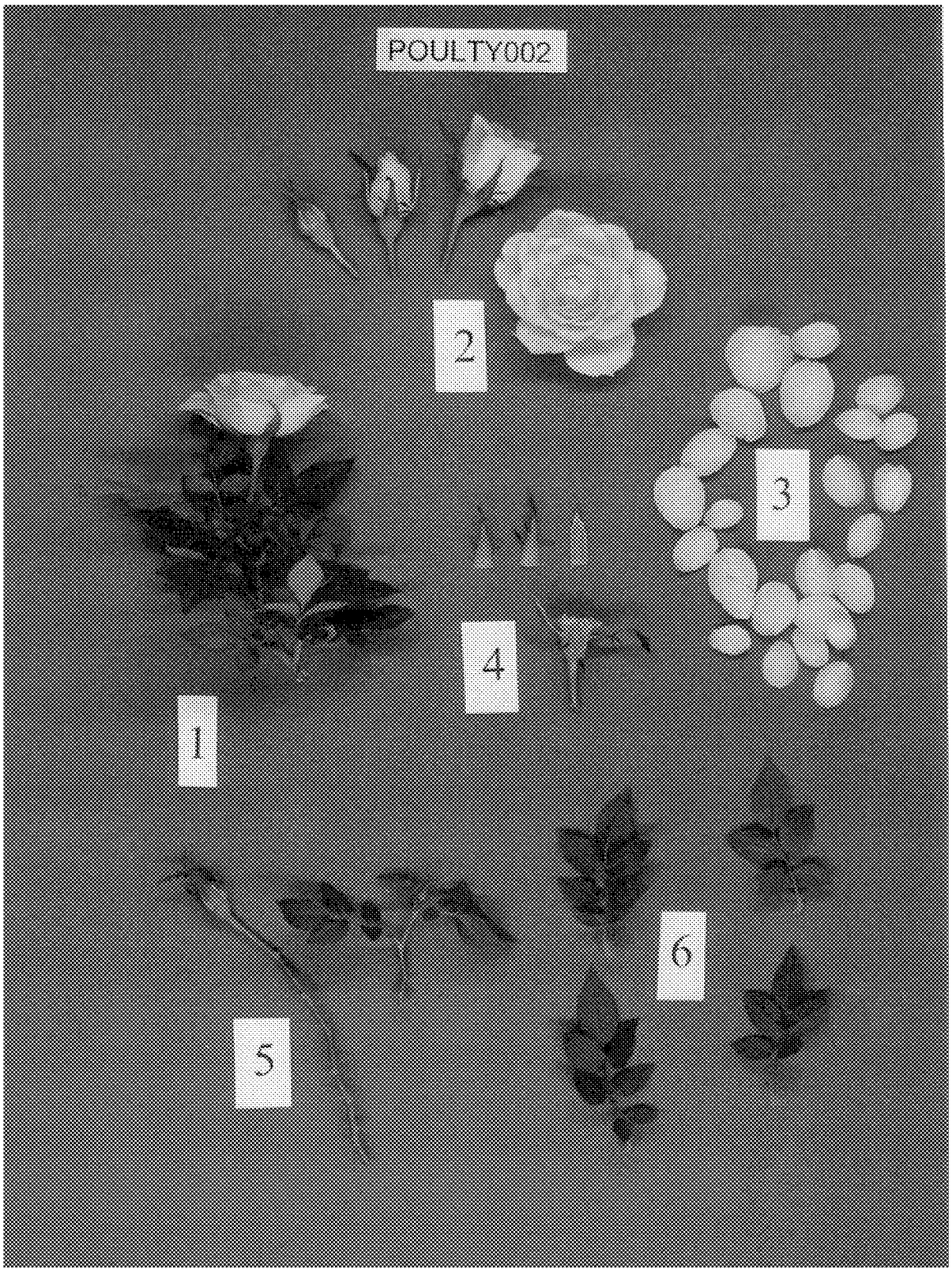
POULTY002
2
3
4
1
6
5